(12) United States Patent
Harrold et al.

(10) Patent No.: US 11,207,004 B2
(45) Date of Patent: Dec. 28, 2021

(54) APPARATUS FOR COLLECTING FINGERPRINTS AND BUCCAL SWABS

(71) Applicant: LIFE TECHNOLOGIES CORPORATION, Carlsbad, CA (US)

(72) Inventors: Michael Harrold, San Mateo, CA (US); Lori Hennessy, San Mateo, CA (US); Leonard Klevan, Cave Creek, AZ (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 16/454,886

(22) Filed: Jun. 27, 2019

(65) Prior Publication Data
US 2019/0385713 A1 Dec. 19, 2019

Related U.S. Application Data

(62) Division of application No. 15/432,915, filed on Feb. 14, 2017, now Pat. No. 10,381,111, which is a
(Continued)

(51) Int. Cl.
*A61B 5/1172* (2016.01)
*G16H 10/60* (2018.01)
(Continued)

(52) U.S. Cl.
CPC .......... *A61B 5/1172* (2013.01); *A61B 5/1174* (2013.01); *A61B 10/0045* (2013.01); *A61B 10/02* (2013.01); *C12Q 1/6806* (2013.01); *C12Q 1/6881* (2013.01); *G06F 16/245* (2019.01); *G06K 9/00013* (2013.01);
(Continued)

(58) Field of Classification Search
CPC .............................. G16H 10/40; C12Q 1/6806
See application file for complete search history.

(56) References Cited

U.S. PATENT DOCUMENTS

| 4,495,149 A | 1/1985 | Iwata et al. |
| 5,876,926 A | 3/1999 | Beecham |

(Continued)

FOREIGN PATENT DOCUMENTS

| WO | WO-2010017299 | 2/2010 |
| WO | WO-2013126824 | 8/2013 |

OTHER PUBLICATIONS

Kopka, et al., "New Optimized DNA Extraction Protocol for Fingerprints Deposited on a Special Self-Adhesive Security Seal and Other Latent Samples Used for Human Identification," Journal of Forensic Science, vol. 56, No. 5, Sep. 2011 pp. 1235-1240.
(Continued)

*Primary Examiner* — Narayan K Bhat
(74) *Attorney, Agent, or Firm* — Workman Nydegger

(57) ABSTRACT

Disclosed are devices and methods for collection, labeling and matching biological samples containing nucleic acid in conjunction with collecting at least one ridge and valley signature such as a fingerprint or footprint of an individual. Such devices and methods are used in forensic, human identification, paternity, tissue typing, and screening technologies to rapidly process an individual's identity, determine the identity of an individual along with the genotype profile of the individual.

18 Claims, 11 Drawing Sheets

Related U.S. Application Data division of application No. 14/380,513, filed as application No. PCT/US2013/027492 on Feb. 22, 2013, now abandoned.

(60) Provisional application No. 61/601,931, filed on Feb. 22, 2012.

(51) Int. Cl.
*G06F 16/245* (2019.01)
*A61B 10/00* (2006.01)
*A61B 5/1174* (2016.01)
*A61B 10/02* (2006.01)
*C12Q 1/6806* (2018.01)
*G06K 9/00* (2006.01)
*C12Q 1/6881* (2018.01)
G16H 10/40 (2018.01)
G16H 40/63 (2018.01)
G16H 30/20 (2018.01)

(52) U.S. Cl.
CPC ......... *G16H 10/60* (2018.01); *A61B 10/0051* (2013.01); *G16H 10/40* (2018.01); *G16H 30/20* (2018.01); *G16H 40/63* (2018.01)

(56) References Cited

U.S. PATENT DOCUMENTS

| | | |
|---|---|---|
| 7,308,123 B2 | 12/2007 | Fenrich et al. |
| 9,058,646 B2 | 6/2015 | Harrold et al. |
| 9,708,644 B2 | 7/2017 | Liu et al. |
| 9,804,066 B2 | 10/2017 | Harrold et al. |
| 2005/0287536 A1 | 12/2005 | Kozlay |
| 2008/0247613 A1* | 10/2008 | Chang ............... G06K 9/00046 382/124 |
| 2009/0227897 A1 | 9/2009 | Wendt et al. |
| 2013/0106568 A1 | 5/2013 | Harrold et al. |
| 2013/0202182 A1 | 8/2013 | Rowe |
| 2015/0031031 A1 | 1/2015 | Harrold et al. |

OTHER PUBLICATIONS

PCT/US2013/027492, Search Report and Written Opinion, dated Jun. 27, 2013, 1-10.

\* cited by examiner

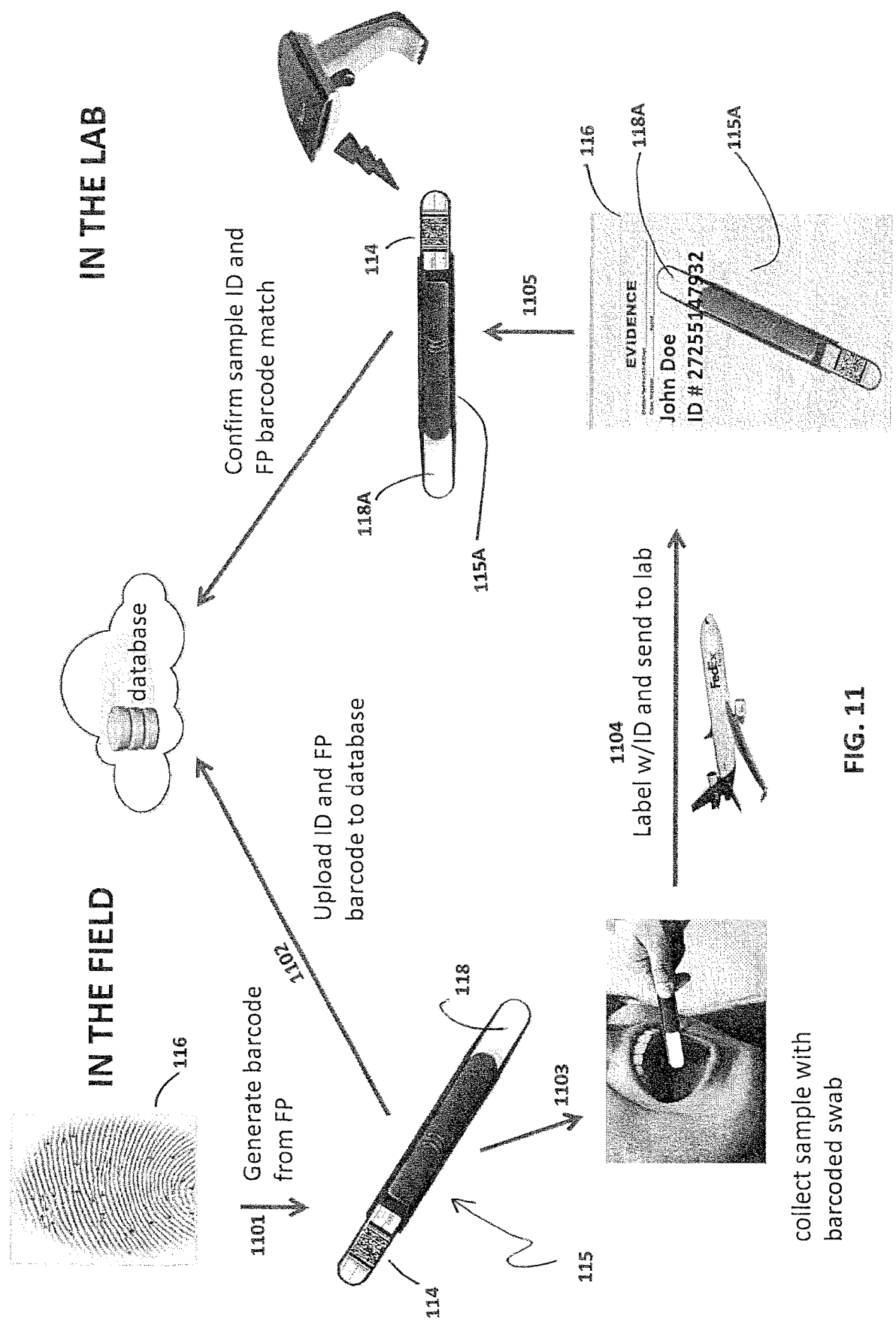
FIG. 1.1

APPARATUS FOR COLLECTING FINGERPRINTS AND BUCCAL SWABS

This application is a divisional of U.S. application Ser. No. 15/432,915 filed Feb. 14, 2017, which is a divisional of U.S. application Ser. No. 14/380,513 filed Aug. 22, 2014 (now abandoned), which is the National Stage of International Application No. PCT/US2013/027492 filed Feb. 22, 2013, which International Application claims the benefit of priority under 35 U.S.C. § 119(e) to U.S. Provisional Application No. 61/601,931 filed Feb. 22, 2012, each disclosure of which is incorporated by reference in its entirety.

The section headings used herein are for organizational purposes only and should not be construed as limiting the subject matter described herein in any way.

FIELD

The present teachings relate to integrated collection systems and methods for linking the identity of the donor of a biological sample with the donor's fingerprints.

INTRODUCTION

Forensic evidence and biometric data are often used together to identify perpetrators of criminal activities as well as for the identification of missing persons, victims of mass disasters, paternity testing and to exonerate the innocent. The ability to simultaneously or concurrently collect biometric characteristic(s) such as fingerprints, an iris or retinal scan, an image or photo of an individual, create an electronic representation of the collected biometric characteristic and associate the representation with a biological sample(s) collected from the individual, such as forensic evidence including but not limited to blood, tissue, hair, body fluid or a buccal sample, provides a system for expediting identification and screening for potential terrorists and felons. Furthermore, maintaining records of biometric characteristic in a database and correlating the representation with the respective biological samples can be complicated at best and susceptible to errors in collecting, manual labeling, cataloging and archiving. Therefore, there remains a need to accurately collect, label and process biometric characteristic(s) and biological samples from a single individual.

SUMMARY

In accordance with the embodiments, there is disclosed a biometric data collection system having a first component adapted to obtain a representation of an appendage of an individual, and at least a second component comprising a substrate adapted to receive a biological sample from the individual, wherein either the substrate or a biological sample collection device comprising the substrate is labeled with the representation. The first component has a surface adapted to obtain an impression of the appendage and an imaging system is operatively coupled to the surface, wherein the imaging system is configured to collect an electronic image resulting from the impression. The imaging system can be either an optical imaging system or a capacitive scanning/imaging system. The collection system can also have a processor configured to convert the electronic image from the impression into the representation of the appendage. Additionally, the processor can provide for and tie the system in with an outside connections module to networks, software sources, databases of such entities as the FBI, Homeland Security, investigative agencies, intelligence agencies, watch lists, cable systems, the web, optical fiber systems, wireless communications such as satellites, cell phone systems (e.g., GSM), and other pertinent resources. Additionally, the processor can have a database connect to the processor and a connection module connected to the processor. The representation can be configured for uploading into a network or database and other pertinent archiving and information retrieval and comparison resources. The system can also have a component adapted to label the substrate or the biological sample collection device with the representation to enable matching the biometric characteristic to the biological sample. The representation can be graphical, digital, photographic, analog, alphanumeric, hexadecimal or binary, including a barcode. The impression obtained by the system can be converted into an electronic image and the appendage can be a finger, thumb, hand, toe or foot placed upon a surface such as a platen that is transparent. The resulting impression can be a fingerprint, thumbprint, handprint, toe print or footprint.

In accordance with the embodiments, there is also disclosed a method for matching collected biometric information comprising: providing a surface for obtaining a representation of an appendage of an individual, wherein an impression of a fingerprint of a finger of the individual is obtained when the individual touches the surface; converting the fingerprint impression to an electronically readable representation; labeling a biological sample collection device with the electronically readable representation; collecting a biological sample from the individual with the labeled biological sample collection device; wherein the electronically readable representation from the fingerprint is matched to the labeled biological sample collection device following collection of the biological sample. The digit can be a finger, thumb, hand, toe or foot placed upon a surface such as a platen that is transparent. The resulting impression can be a fingerprint, thumbprint, handprint, toe print or footprint. The biological sample can be analyzed by genotyping or HLA typing and the collected biometric information can be archived in a database, network or other pertinent resource.

In accordance with the embodiments, there is also disclosed a method for matching collected biometric information comprising: providing a surface for obtaining a representation of an appendage of an individual, wherein an impression of the appendage of the individual is obtained when the individual touches the surface, wherein the appendage is a digit; converting the impression to an electronically readable representation; labeling a substrate with the electronically readable representation; transferring a biological sample from the individual to the substrate; and matching the electronically readable representation from the impression to the labeled substrate following collection of the biological sample. The digit can be a finger, thumb, hand, toe or foot placed upon a surface such as a platen that is transparent. The resulting impression can be a fingerprint, thumbprint, handprint, toe print or footprint. The biological sample can be analyzed by genotyping or HLA typing and the collected biometric information can be archived in a database, network or other pertinent resource.

In the following description, certain aspects and embodiments will become evident. It should be understood that a given embodiment need not have all aspects and features described herein. It should be understood that these aspects and embodiments are merely exemplary and explanatory and are not restrictive of the invention.

The accompanying drawings, which are incorporated in and constitute a part of this specification, illustrate several exemplary embodiments of the disclosure and together with the description, serve to explain certain teachings.

There still exists a need for improved systems and methods for obtaining biometric data and biological sample of individuals, while retaining proper matching between samples and the biometric data. Therefore, it is desirable to develop systems and methods which provide a higher assurance of identity between a given biological sample and biometric data associated with the biological data. The systems and methods described herein fulfill that need to provide higher certainty that a sample associated with a specific individual actually is that sample and not that of another individual.

These and other features of the present teachings are set forth herein.

BRIEF DESCRIPTION OF THE DRAWINGS

The skilled artisan will understand that the drawings described below are for illustration purposes only. The drawings are not intended to limit the scope of the present teachings in any way.

FIG. 11 is a schematic representation of one embodiment of the method for authenticating a collection swab 115 containing a substrate 118. An impression of an appendage 116 may be obtained in the field or point of contact, and in step 1101, a barcode 114 or other representation is generated from the impression or an image thereof. The barcode and identifying information is uploaded to a remote database (unnumbered) in step 1102. In step 1103, a biological sample is deposited to the substrate that is labeled with the barcode 94, and optionally the image 96 of the impression and other identifying information 96a. In step 1104, the archival sample card is transported to a central laboratory. In step 905, the barcode 114 and identifying information 115a is read by suitable means. The remote database is interrogated to determine whether the sample ID 96a and barcode 94 matches the data input in the field or point of contact. After authentication, the substrate 118a containing the biological sample is processed and tested in one or more assays.

Figure 1:
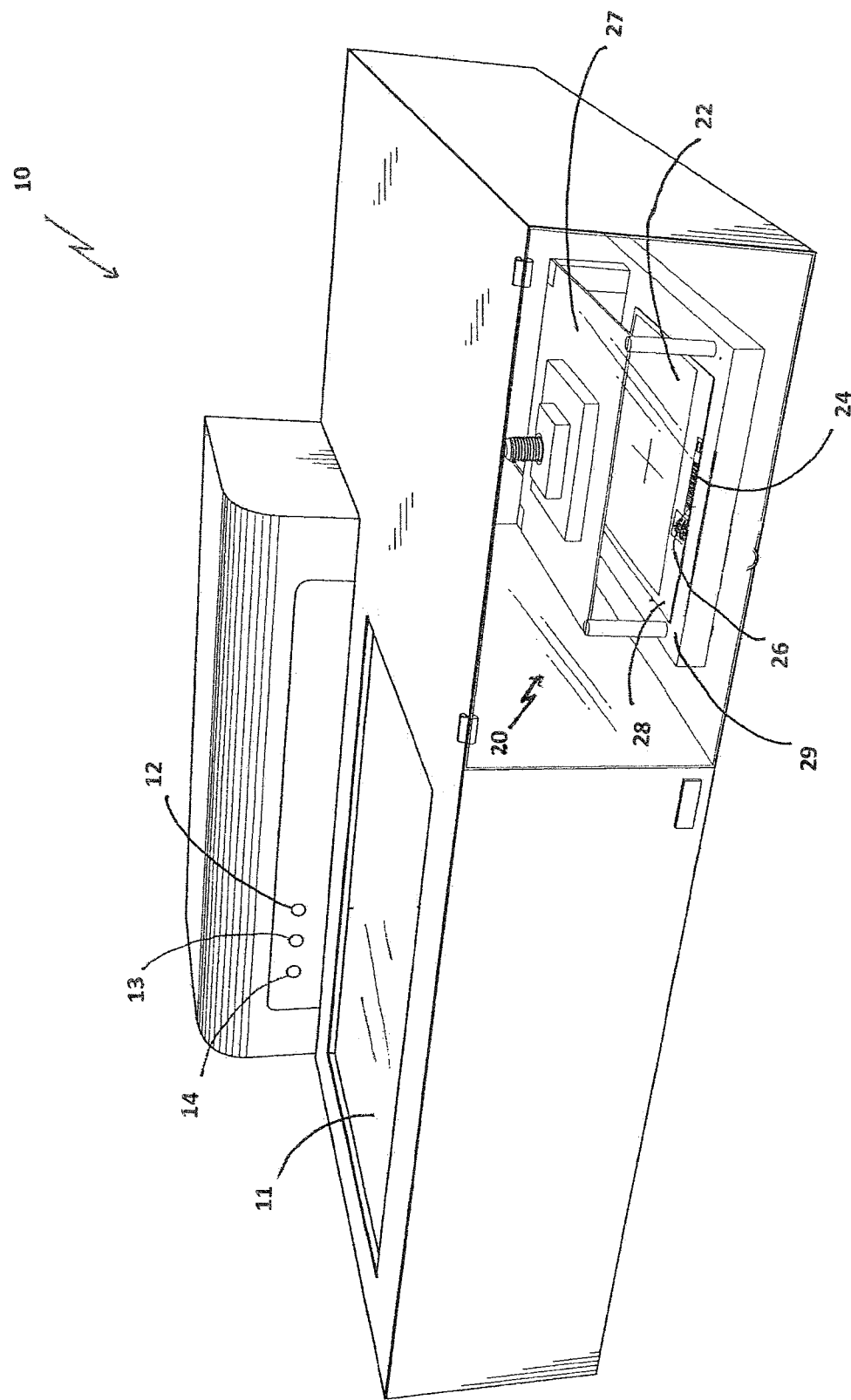
FIG. 1 is a schematic representation of one embodiment of the biometric system 10 disclosed herein. A surface 11 captures an impression of an appendage. Ports 12, 13 and 14 can have a photo-capturing component, a sensor component and motion sensor component, respectively. Operatively coupled to surface 11 is a biological sample collection system 20. A collected biological sample, including but not limited to a swab, is placed on a substrate 28. The substrate is labeled with a barcode representation 24 and fingerprint representation 26. The substrate is covered by a protective film 22. The substrate 28 is positioned on a heat block 29 and the biological sample containing substrate can be sealed by the application of pressure from press 27.
Figure 2:
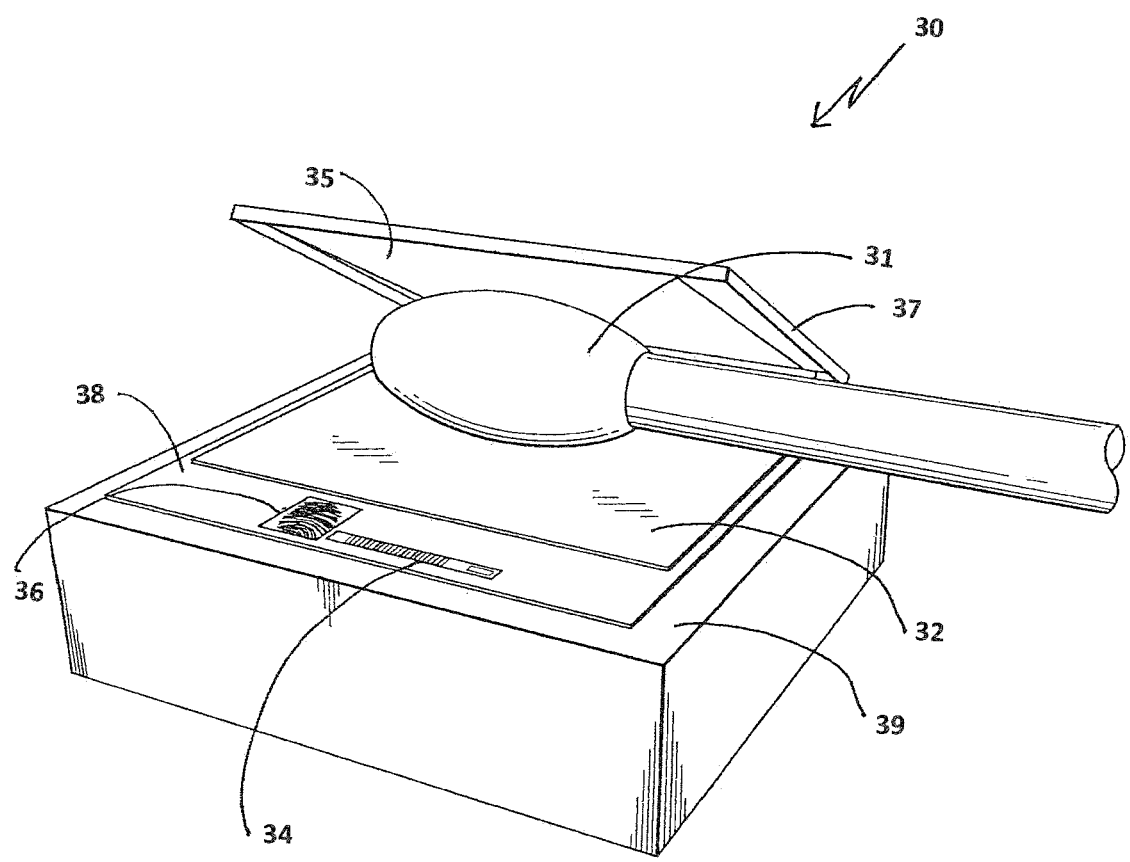
FIG. 2 is a schematic representation of one embodiment of the method for processing a biological sample. The biological sample collection system 20 has swab 31 pressed upon a substrate 38. The substrate is labeled with a barcode representation 34 and fingerprint representation 36. The substrate is covered by a protective film 32. The substrate 38 is positioned on a heat block 39 and the biological sample containing substrate can be sealed by the application of pressure from press 37 shown with film 35.
Figure 3:
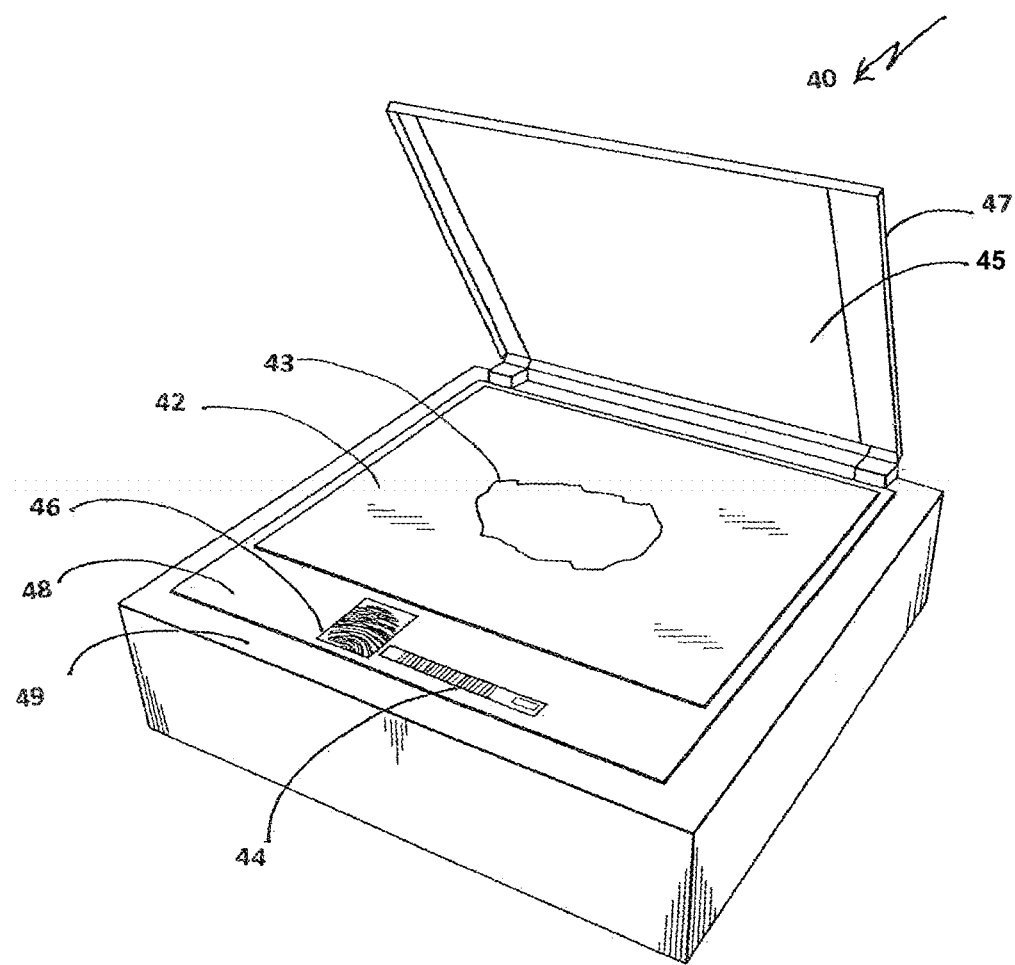
FIG. 3 is a schematic representation of one embodiment of the method for processing a biological sample. The biological sample collection system 40 biological sample 43 pressed upon a substrate 48. The substrate is labeled with a barcode representation 44 and fingerprint representation 46. The substrate's biological sample 43 is covered by protective film 42. The substrate 48 is positioned on a heat block 49 and the biological sample containing substrate can be sealed by the application of pressure from press 47 shown with weight 45.
Figure 4:
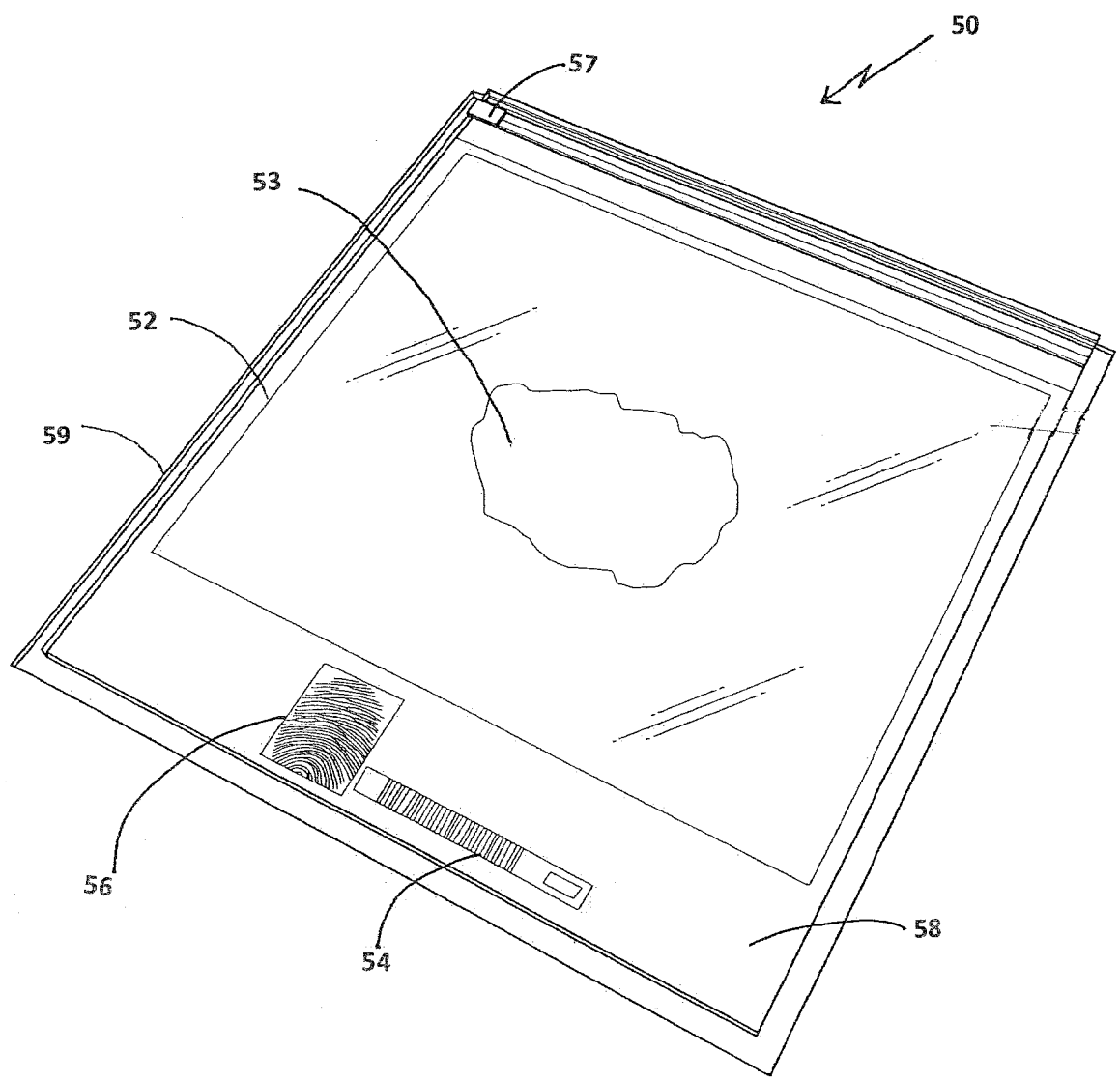
FIG. 4 is a schematic representation of one embodiment of the matched fingerprint 56 and biological sample 53 following the disclosed methods for processing a biological sample. The biological sample collection system 50 has biological sample 53 pressed upon a substrate 58. The substrate 58 is labeled with a barcode representation 54 and fingerprint representation 56. The substrate's biological sample 53 is covered by protective film 52. The substrate 58 and the biological sample 53 are sealed 57 in a protective pouch 59.
Figure 5:
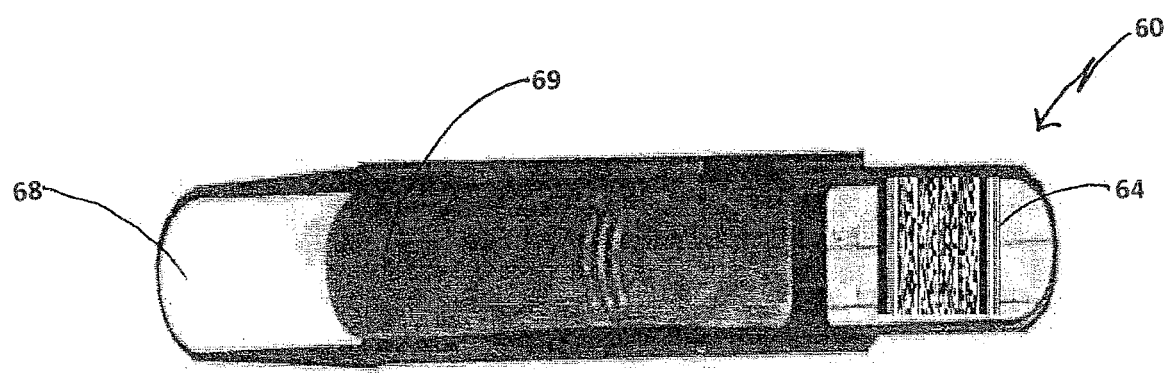
FIG. 5 is a schematic representation of one embodiment of a biological sample collection device 60. A substrate 68 enclosed and attached to the device lies at one end of said device 60 and is composed of either treated paper e.g., Whatman® FTA paper (Whatman) or untreated paper (e.g. 903 paper). The substrate 68 is protected by cover 69 prior to collection and after collection of a biological sample to preclude contamination by extraneous nucleic acids, environmental contaminants and the like. A label having the barcode representation 64 derived from the fingerprint of the same individual who provided the biological sample is at the opposite end of device 60. Additional information such as name, date of birth, and so on can be further added to the collection device 60.
Figure 6:
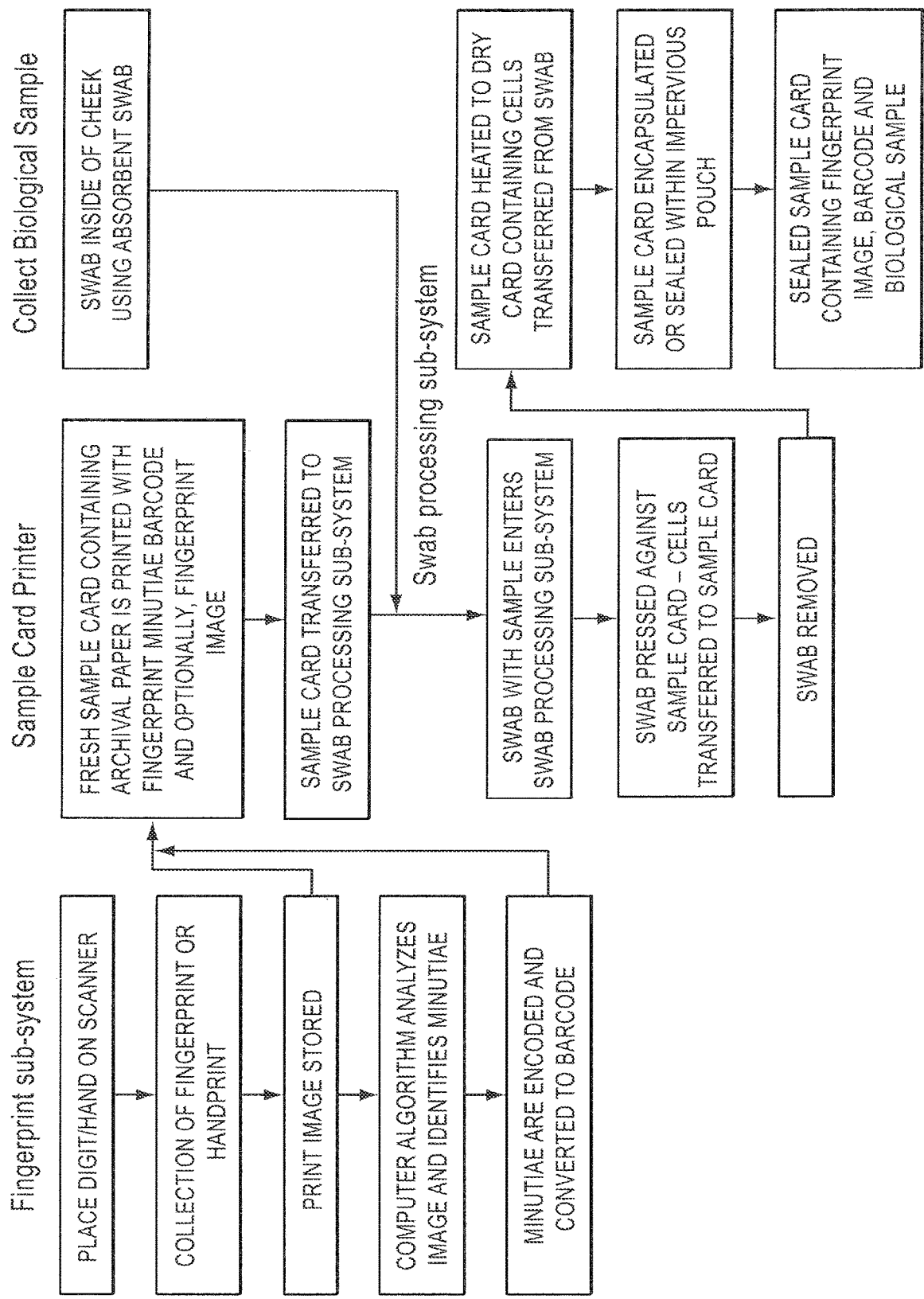
FIG. 6 is a schematic representation of one embodiment of a workflow of the disclosed systems and methods.
Figure 7:
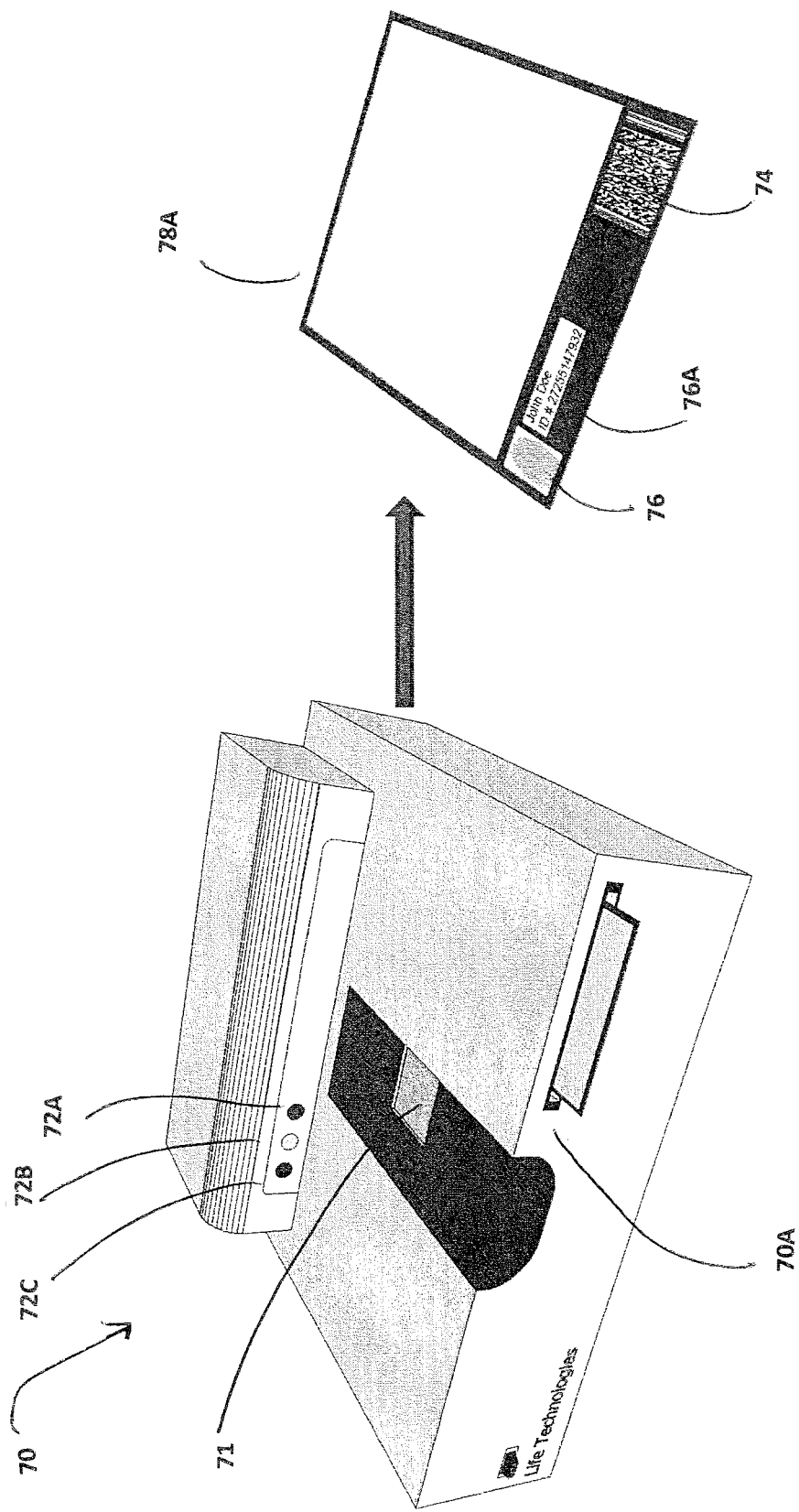
FIG. 7 is a schematic representation of an embodiment of the biometric system 70 disclosed herein. A surface 71 captures an impression of an appendage. Ports 72a, 72b, and 72c can have a photo-capturing component, a sensor component and motion sensor component, respectively. Operatively coupled to surface 71 is the biometric collection and data processing system 70. After processing, an image of the impression 76, a barcode representation 74 of the impression, and, optionally, further identifying information 76a (ie. personal name, other identifying code numbering, etc) is deposited on a substrate 28.
Figure 8:
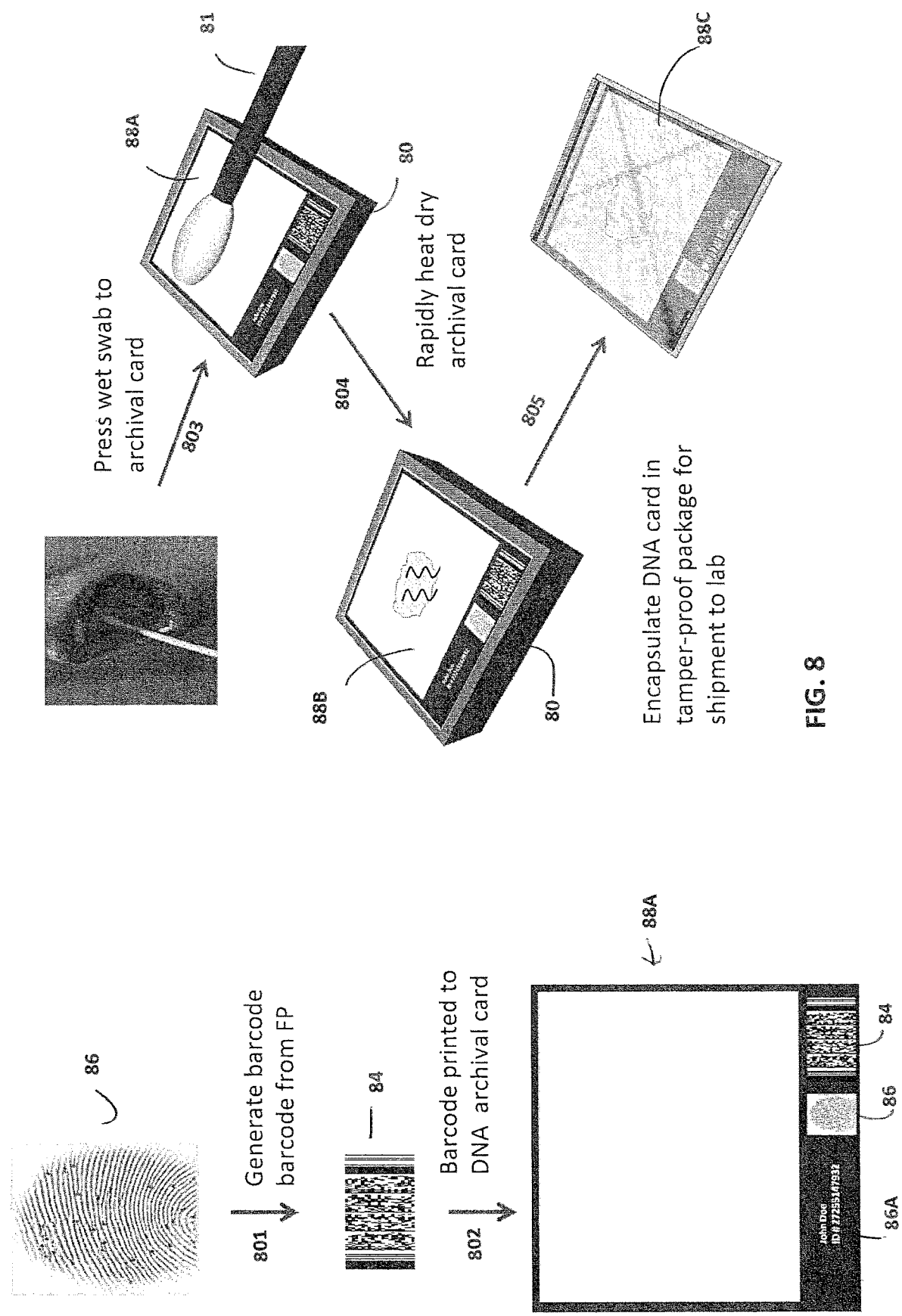
FIG. 8 is a schematic representation of one embodiment of the method for processing a biological sample. An impression of an appendage 86 is obtained, and in step 801, a barcode 84 or other representation of the impression is generated. In step 802, a substrate 88A is labeled with barcode 84, other identifying information 86a, and optionally, with impression 86. In step 803, biological sample, obtained with swab 81, is transferred to substrate 88A. In some embodiments, the substrate is already in place on an apparatus 80. In step 804, apparatus 80 dries the archival card bearing the biological sample to produce the dried sample on substrate 88B. In step 805, the archival card is encapsulated 88C in a tamper-proof package for transport to a testing facility. The image 86 of the impression of the appendage or the barcode 84 representation of the impression may be used to authenticate the archival card bearing the biological sample.
Figure 9:
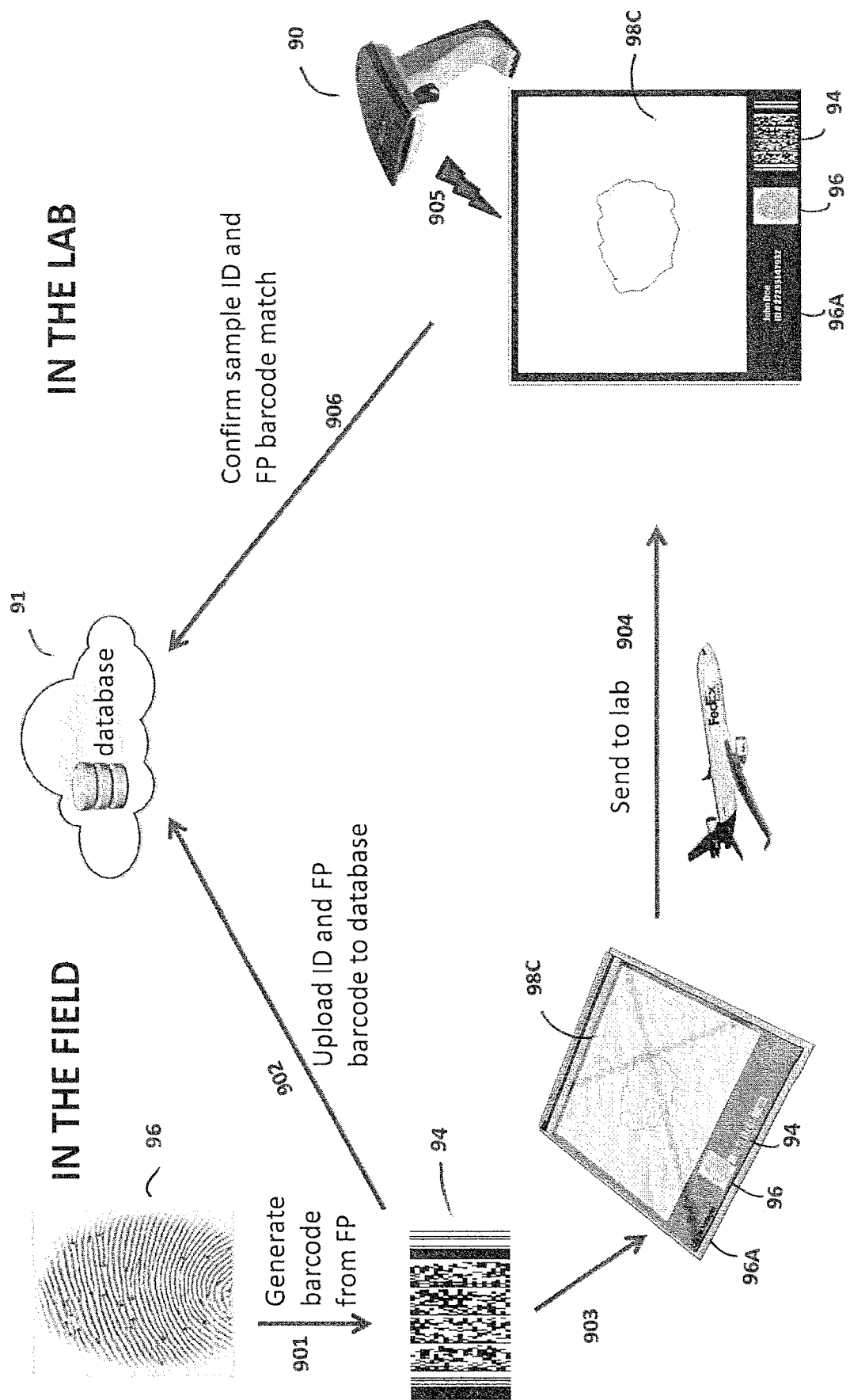
FIG. 9 is a schematic representation of one embodiment of the method for authenticating the archival card containing the biological sample bearing substrate, which may or may not be sealed in protective covering or envelope. An impression of an appendage 96 may be obtained in the field or point of contact, and in step 901, a barcode 94 or other representation is generated. The barcode and identifying information is uploaded to a remote database 91 in step 902. In step 903, a biological sample is deposited to the substrate that is labeled with the barcode 94, and optionally the image 96 of the impression and other identifying information 96a, and the archival sample card 98C is sealed for protection. In step 904, the archival sample card is transported to a central laboratory. In step 905, the barcode 94, identifying information 96a, and, optionally, the image 96 of the impression is read by suitable means. The remote database 91 is interrogated to determine whether the sample ID 96a and barcode 94 matches the data input in the field or point of contact.
Figure 10:
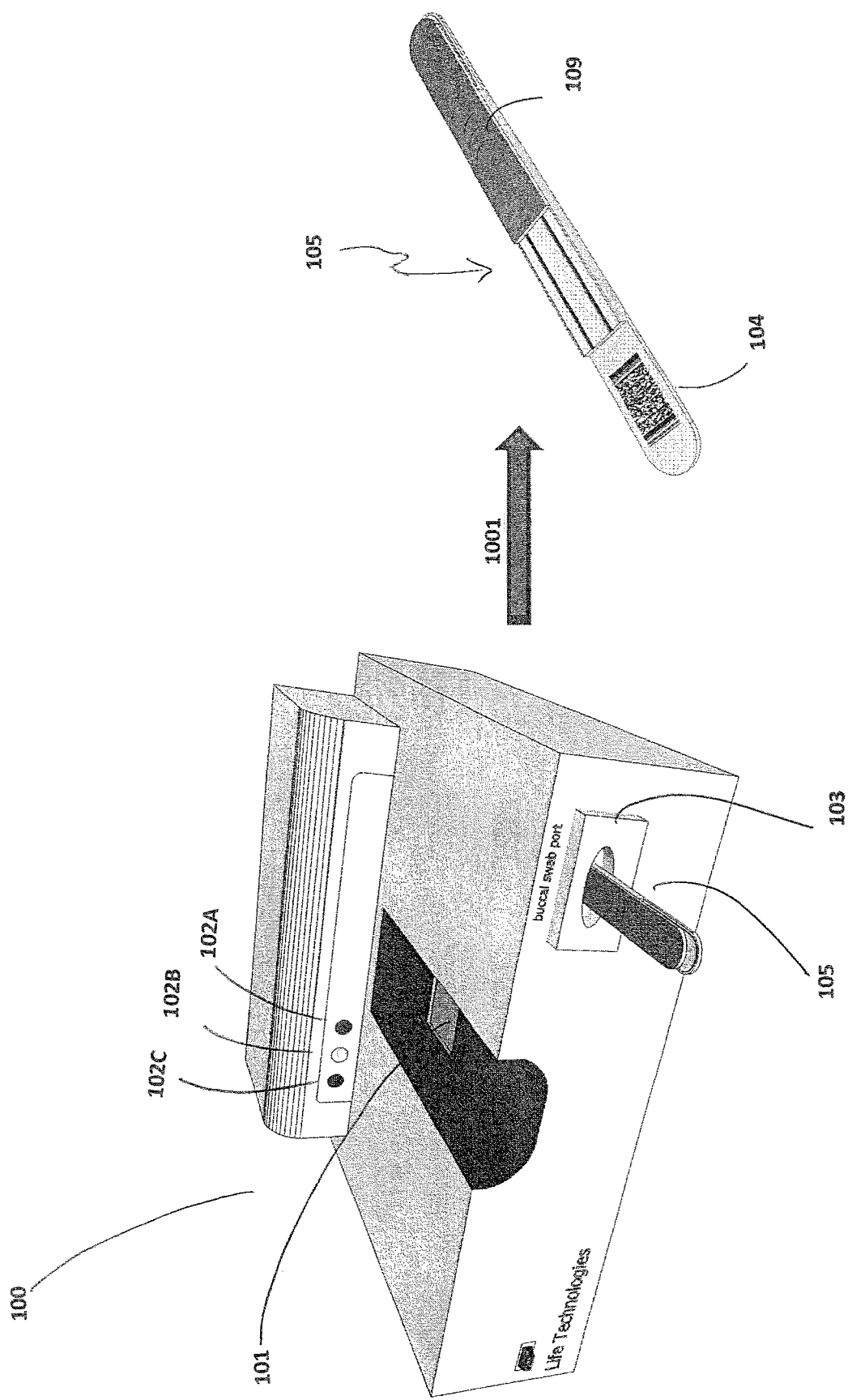
FIG. 10 is a schematic representation of an embodiment of the biometric system 100 disclosed herein. A surface 101 captures an impression of an appendage. Ports 102a, 102b, and 102c can have a photo-capturing component, a sensor component and motion sensor component, respectively. Operatively coupled to surface 101 is the biometric collection and data processing system 100. After processing, a barcode representation 74 of the impression, and, optionally, further identifying information 76a (ie. personal name, other identifying code numbering, etc) is labeled in a swab labeling port 103 on collection swab 105. Collection swab 105 may further have a cover 109, protecting the collection substrate surface.

It is to be understood that the figures are not drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the last two digits of reference numbers will be used throughout the drawings to refer to the same or like parts.

DETAILED DESCRIPTION

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

Repeated usage of the phrase "in one embodiment" does not necessarily limit to usage to that same embodiment, although it may.

Unless otherwise defined, scientific and technical terms used in connection with the present teachings described herein shall have the meanings that are commonly understood by those of ordinary skill in the art. Generally, nomenclatures utilized in connection with, and techniques of, molecular biology, and oligo- or polynucleotide chemistry and amplification and detection thereof described herein are those well known and commonly used in the art.

As used herein, the phrase "membrane," "partition," "layer," and "film" are interchangeable and not intended to be limiting.

As used herein, the phrase "nucleic acid," "oligonucleotide", and polynucleotide(s)" are interchangeable and not intended to be limiting.

"Biometric data" as used herein, refers to data related to physiological aspects of an individual and may include skin recognition, including but not limited to fingerprints and palm prints; body geometry features, including but not limited to ear, hand, finger, and the like; facial features; face images; voice; voice prints; optical recognition, including but not limited to iris scans and retinal scans; signatures; blood typing; nucleic acid profiles, including deoxyribonucleotide (DNA) profiles and ribonucleic acid (RNA) profiles; protein assays; infrared identification, including but not limited to face, hand, and hand vein; and the like. One or more of these may be used in any combination.

DNA data include but are not limited to Short Tandem Repeat (STR); Single Nucleotide polymorphism (SNP); Insert and Deletion (INDEL) sequences; Alu elements and other non-STR repeat sequences. In some embodiments, the DNA data is any polymorphic DNA sequence that can be used for human identification.

STR profile: Common sets of short tandem repeat (STR) markers or "core loci" permits equivalent genetic information to be shared and compared. These core STR loci occur in between genes where a high degree of variability is tolerated and are thus not directly responsible for physical traits or genetic diseases. The "core loci" are often used in human identity testing such as parentage testing and missing persons and mass disaster investigations, as well as for entry of DNA genotype data into national or international databases used to link serial crimes and offenders. Presently, the FBI has generated 13 core STR loci as the basis for the genetic fingerprinting of an individual and maintains a database of such information for later reference. Other international organizations focus on different, but overlapping sets of STR loci, as shown in Table 1. One of skill can determine that additional loci may be useful to add to a STR profile, and the listing herein is by no means limiting.

SNP profile: Single nucleotide variants in a DNA sequence may be in coding, non coding or intergenic regions of genes, differing between members of a biological species or between paired chromosomes of an individual. Some SNP sequences may be related to phenotypic characteristics of an individual. This data may be of particular use if attempting to interrogate data where there is incomplete personal information for a biometric data set.

INDEL profile: Insertion and deletion sequences include the following types of insertion/deletions: insertions or deletions of single base pairs; expansions by only one base pair (monomeric base pair expansions); multi-base pair expansions of about 2 to about 15 repeats; transposon insertions (insertions of mobile elements); and random DNA sequence insertions or deletions.

Alu element: Alu elements are mobile and repetitive elements in the human genome. Alu elements are generally about 300 bp and are considered as a short interspersed element (SINE) within the broad class of repetitive DNA elements. Derived from the small cytoplasmic 7SL RNA, these inserted elements are interspersed throughout the genome. About 7,000 Alu elements are unique to humans, and some may result in disease. Alu elements are useful in human identification as Alu element insertion events have characteristic signatures and reveal details of ancestry and relatedness.

"Hash", "hashed" or "hashing" as used herein, refers to data transformation which converts variable sized data to another representation. "Hash" as used herein, includes usage as both verb and noun forms. For example, a hash can be the representation resulting from the data transformation. The representation may be of fixed data size, same data size, different data size or variable data size. The representation may be of the same data type or another data type, including but not limited to numerical, alphabetical, graphical, or audio. The graphical representation may be pictorial or schematic, including but not limited to a barcode representation. The representation may be encrypted. The encrypted representation may be invertible with or without a key, or the encrypted representation may be encrypted one-way.

Many forms of data transformation are useful in this invention. In some of the embodiments of the invention, the hashing produces the same end value for a given input data every time the hash is produced. The hashing also provides unique values for unique input, thus providing uniform distribution of the hash values within a potential range, and preventing differing input biometric data from mapping to the same hash value. One of skill can determine other data manipulation that may be useful for storage of the hash values as enrollment databases enlarge.

Some useful cryptographic hash functions include BLAKE-256, BLAKE-512, ECOH, FSB, GOST, Grostl, HAS-160, NAVAL, JH, Keccak, MD2, MD4, MD5, MD6, RadioGatún, RIPEMD-64, RIPEMD-160, RIPEMD-320, SHA-0, SHA-1, SHA-224, SHA-256, SHA-384, SHA-512, Skein, Snefru, Spectral Hash, SWIFFT, Tiger, and Whirlpool.

An additional level of data transformation may be used to verify data integrity and to authenticate the hash values represented on an identification card of the invention. A Hash-based Message Authentication Code (HMAC) may be used to combine the cryptographic hash functions described above with a secret key. One definition of the HMAC algorithm from a source, RFC 2014 code, defines the algorithm as follows: H(·) is a cryptographic hash function K is a secret key, for example, padded to the right with extra zeros to the input block size of the hash function, or the hash of the original key if it is longer than that block size;
m is the message to be authenticated;
∥ denotes concatenation;
⊕ denotes exclusive or (XOR);
opad is the outer padding (0x5c5c5c . . . 5c5c, one-block-long hexadecimal constant);
ipad is the inner padding (0x363636 . . . 3636, one-block-long hexadecimal constant);
Then HMAC(K,m) can be mathematically defined as: HMAC(K,m)=H((K⊕opad)∥H((K⊕ipad)∥m)), in one non-limiting example. The cryptographic strength of the HMAC depends upon the size of the secret key that is used. The most common attack against HMACs is brute force to uncover the secret key. HMACs are substantially less affected by independent values mapping to the same hash values, i.e. collisions, than their underlying hashing algorithms alone. Therefore, HMAC-MD5 does not suffer from the same weaknesses that have been found in MD5, for example.

Hashing methods allowing some degree of dissimilarity while still finding identity between two substantially similar files, are widely available and are often referred to as fuzzy hash functions. Context triggered piecewise hashing is one method of matching not quite identical sets of bits of information. An example of such a method combines a rolling hash with a piecewise hash, as devised by Kornblum (Kornblum, Digital Investigation 3S (2006), pp S91-S97). Other fuzzy hashing tools include ssdeep and deeptoad. Additionally, fuzzy hash algorithms are disclosed in U.S. Patent Application Publications 2011/0093426 and 2011/0067108 (Hoglund), for classifying data objects including DNA sequences.

In some embodiments of the invention, hashing methods are used that allow a predetermined degree of dissimilarity when comparing two hashes for identity. Even a small change, for example, in orientation of a fingerprint scan, may provide a digitized form that yields a different hash from a different fingerprint scan taken from the same finger at a different time, location or after a degree of physiological modification. These hashing methods can be useful when differences in the source or target biometric data do not provide an exact match but do possess a degree of similarity high enough for a positive identification. Therefore, the processor may be instructed to not require perfect identity to signal a match. DNA profiles may also demonstrate some dissimilarity upon hashing, but still be capable of being detected by the processor as representing a reasonable match. Allowing some degree of dissimilarity while still determining that a match has been identified, can initiate a further inquiry into the identity of the individual presenting the identification card.

The description also uses the terms such as "secure," "protected," "encrypted," "authenticated," etc. These terms refer to a given level of security, protection, authenticity, etc.

The disclosed system concurrently or consecutively collects biometric information and at least one biological sample. At some points of entry such as international airports, customs, port authorities, border crossings, money-supplying bank kiosks, admission to secure areas, it is important to positively identify the person seeking entry. The present system may use a series of techniques for identifying such a person. The present system can also be utilized to ensure chain of custody, database work, casework sample processing, cataloging individuals for tissue registries for both donors and recipients, individual identification and for paternity testing.

The resulting information can be acted upon, such as with searching and comparison with databases, and processing in seeking an independent verification of identity of the person providing the appendage impression and the at least one biological sample. The data collection may be short-term and utilized for just identification at the moment of collection, or the collection may be a basis for building an identification database or databank, and/or for long-term storage and analysis. The present system may detect a user who is attempting to provide false identification and/or information or a person crossing an international boarder without proper authorization. The collection of such data and associated activities may be covert, partially covert, or not covert. Incidentally, there may be laws in certain jurisdictions that regulate the collection and use of certain kinds of biometric data.

The disclosed system will identify an individual who may have participated in an act of violence or terrorism previously without additionally encompassing innocent individuals who have some characteristics in common, such as name or physical description.

Additionally, while biometric data are useful personal identifiers, it is also desirable to prevent unauthorized access or theft of such data. Unlike passwords and the like, individualized biometric data cannot be revoked and reissued after a breach of security.

There are a number of databases being managed and developed by agencies who gather evidence from attempted or successful acts of violence and terrorism, which include biometric data including, without limitation, fingerprints, voice recordings, DNA samples from which DNA data may be developed, and the like, which are entered into the database.

It is of interest to be able to interrogate these databases to identify individuals who may request access to an entity, transport, information, location, transaction, services, authorized status, funds, and the like, but who may be at high risk of attempting acts of violence or terrorism. Additionally, it would be useful to definitively verify the identity of an individual who is legitimately requesting access to an entity, international boarder, transport, information, location, transaction, services, authorized status, funds, and the like.

The individualized identification information includes individualized biometric data of at least a first class and a second class, where the individualized biometric data of the first class and the individualized biometric data of the second class has been stored on the card as a hash formed from the individualized biometric data of the first and second class. The individualized identification information may further include a third class of individualized biometric data or more. The third and additional classes of individualized biometric data may be present on the identification card in a hashed form, and may be invertible. The third and additional classes of individualized biometric data may be present on the identification card in a non-invertible hashed form.

In some embodiments of the invention, the biometric data is selected from the group consisting of a fingerprint scan data, a palm print scan data, a retinal scan data, an iris scan data, or a hand vein scan data of the individual. In some embodiments the biometric data is a biological sample for which genetic and/or genotyping data can be obtained. Such data includes a DNA data, including a STR profile, SNP profile, or INDEL profile, an Alu element, a non-STR DNA profile, or a fingerprint scan of the individual. In other embodiments the biometric data a DNA data, including a STR profile, SNP profile, or INDEL profile, an Alu element, or a non-STR DNA profile of the individual.

In some embodiments, a biometric data collection system is disclosed as illustrated in FIG. 1. The system provides a first component which collects an impression of an appendage such as a fingerprint, handprint or toe print from an individual. The impression is processed into an electronic image in a format suitable for uploading into a database or network.

In some embodiments, the system provides a first component which collects an impression of an appendage such as a fingerprint, handprint or toe print from an individual. The system may include a second component which is configured to process the impression to form an electronic image having a format suitable for uploading into a database or network. The electronic image can be converted into a representation including but not limited to a graphical, digital, photographic, analog, alphanumeric, hexadecimal or binary representation which can be represented as a hash or barcode. The representation may be used to label the biological sample obtained in the methods described herein or to label containers, substrates, collection devices or data associated with the subject providing the impression.

In some embodiments, the first component includes an optical imaging system. In other embodiments the apparatus can comprise a first solid-state ridge and valley signature reader. Ridge and valley signatures can be distinguished by optical, ultrasonic, capacitive or thermal means using an analog means as well as by a touchless three-dimensional ridge and valley scanners using a digital processing means. (Wang, Yongchang; Q. Hao, A. Fatehpuria, D. L. Lau and L. G. Hassebrook (2009). "Data Acquisition and Quality Analysis of 3-Dimensional Fingerprints". Florida: IEEE conference on Biometrics, Identity and Security. http://vis.uky.edu/~realtime3d/Doc/3D_Fingerprint_Quality.pdf. Retrieved March 2010. Wang, Yongchang; D. L. Lau and L. G. Hassebrook (2010). "Fit-sphere unwrapping and performance analysis of 3D Fingerprints". Applied Optics. pp. 592-600. The optical imaging system has an illuminating means for optically collecting the ridge and valley signature using an optical scanner as is known to one of skill in the art. The optical scanner can be an array of a plurality of light emitting diodes or a multispectral illuminator. In an optical scanner a beam of light passes through the topological impression made by the test subject upon exposure to the source of illumination wherein the test subject places the finger, hand, palm, toe, sole or foot against a surface of the imaging system having an illuminating source. In one embodiment the surface comprises a platen, wherein the platen is transparent to allow the illuminating source to illuminate the at least one valley and ridge of the test subject. After collection of the at least one ridge and valley signature, the signature, in analog or digital format can be transmitted to a database having a plurality of ridge and valley signatures as well as other physical biometric data. In some embodiments, the collection of data includes minutia. In certain embodiments the illumination source is from LEDs, laser diodes, incandescent sources, or a multispectral imager. The illumination may include light of a combination of wavelengths, and may be made from more than one angle of illumination relative to the platen and/or appendage being scanned. The illumination may include light that is coherent or noncoherent, polarized or non polarized, and may have wavelengths from near ultraviolet (320-400 nm) to mid-infrared (approximately 5 microns). In some embodiments, the resulting images are significantly affected by the presence and distribution of total-internal-reflectance ("TIR") phenomena at the interface between the platen and the appendage. In other embodiments, the resulting image of the appendage is substantially unaffected by the presence or absence of TIR effects at the platen. In some embodiments, the light collected from the illuminated surface may include light reflected at the surface of the skin. In other embodiments, the light collected may include light reflected from subsurface scattering from beneath the surface of the skin. Such subsurface scattered light may yield more robust images when impressions of appendages are made under sub-ideal circumstances.

Any suitable instrumentation may be used to acquire the image of an appendage according to the methods described herein. Some instruments and techniques include but are not limited to those disclosed in U.S. Pat. Nos. 4,537,484, 6,175,407, 6,665,427, 8,014,581, 8,036,431, 5,177,353, 6,282,303, 6,188,781, 6,741,729, 6,122,394, 6,826,000, 6,496,630, 6,628,813, 6,983,062, 7,162,060, 7,164,440, 7,657,067, 8,073,209, 7,190,817, 7,558,410, 7,565,541, 7,995,808, 7,899,217, 7,890,158, 7,835,554, 7,831,072, 7,819,311, 7,804,984, 7,801,339, 7,801,338, 7,751,594, 7,735,729, 7,668,350, 7,627,151, 7,620,212, 7,613,504, 7,545,963, 7,539,330, 7,508,965, 7,460,696, 7,440,597, 7,394,919, 7,386,152, 7,347,365, 7,263,213, 7,203,345, 7,147,153, 6,816,605, 6,628,809, 6,560,352, US20110235872, US20110211055, US20110165911, US20110163163, US20110085708, US20100246902, US20100067748, US20090245591, US20090148005, US20090092290, US20090080709, US20090046903, US20080304712, US20080298649, US20080297788, US20080232653, US20080192988, US20080025580, US20080025579, US20070116331, US20070030475, US20060274921, US20080244947, US20060210120, US20060202028, US20060110015, US20060062438, US20060002598, US20060002597, US20050271258, US20050265586, US20050265585, US20050205667, US20050185847, US20050007582, US20040240712, US20040047493, US20030223621, US20030078504, US20020183624, and US20020009213, each of which is herein incorporated by reference in its entirety.

The electronic image can be converted into a representation including but not limited to a graphical, digital, photographic, analog, alphanumeric, hexadecimal or binary representation which can be represented as a hash or barcode. The system has at least a second component including a substrate adapted to receive a biological sample from the individual. The biometric system labels either the substrate or a biological sample collection device comprising the substrate with the representation derived from the electronic image from the first component. The first component has a surface adapted to obtain an impression of the appendage. The surface can be a platen, a film or other material capable of being scanned or photographed by an imaging system, either optically or capacitively. The imaging system is operatively coupled to the surface, wherein the imaging system is configured to collect an electronic image resulting from the impression.

In some embodiments, the collection system can also have a processor configured to convert the electronic image acquired from the impression into the representation of the appendage. Additionally, the processor can provide for and tie the system in with an outside connections module to networks, software sources, databases of such entities as the FBI, Homeland Security, investigative agencies, intelligence agencies, watch lists, cable systems, the web, optical fiber systems, wireless communications such as satellites, cell phone systems (e.g., GSM), and other pertinent resources. Additionally, the processor can have a database connect to the processor and a connection module connected to the processor. The representation can be configured for uploading into a network or database and other pertinent archiving and information retrieval and comparison resources. The system can also have a component adapted to label the substrate or the biological sample collection device with the representation to enable matching the biometric characteristic to the biological sample. The representation can be graphical, digital, photographic, analog, alphanumeric, hexadecimal or binary, including a barcode. The impression obtained by the system can be converted into an electronic image and the appendage can be a finger, thumb, hand, toe or foot placed upon a surface such as a platen that is transparent. The resulting impression can be a fingerprint, thumbprint, handprint, toe print or footprint.

In further embodiments, there is also disclosed a method for matching collected biometric information. The method utilizes a surface for obtaining a representation of an appendage of an individual. The representation results when an individual places an appendage, including but not limited to a finger on the surface. The finger imparts an impression when the individual touches the surface. The fingerprint impression is scanned by an imaging system operatively coupled to the surface. The imaging system converts the image into an electronically readable representation. The representation, as a label, is imprinted on to a biological sample collection device. The electronically readable representation can be read by a scanner, lazar scanner, and barcode reader and so on. The biological sample collecting device can collect a biological sample from the individual with the labeled biological sample collection device. A technician or designated security personal can compare the representation on the collection device following collection with the fingerprint representation to verify the biological sample matches the individual whose fingerprint was used to generate the representation. The digit can be a finger, thumb, hand, toe or foot placed upon a surface such as a platen that is transparent. The resulting impression can be a fingerprint, thumbprint, handprint, toe print or footprint. The biological sample can be analyzed by genotyping or HLA typing and the collected biometric information can be archived in a database, network or other pertinent resource.

In accordance with the embodiments, there is also disclosed a method for matching collected biometric information comprising: providing a surface for obtaining a representation of an appendage of an individual, wherein an impression of the appendage of the individual is obtained when the individual touches the surface, wherein the appendage is a digit; converting the impression to an electronically readable representation; labeling a substrate with the electronically readable representation; transferring a biological sample from the individual to the substrate; and matching the electronically readable representation from the impression to the labeled substrate following collection of the biological sample. The digit can be a finger, thumb, hand, toe or foot placed upon a surface such as a platen that is transparent. The resulting impression can be a fingerprint, thumbprint, handprint, toe print or footprint. The biological sample can be analyzed by genotyping or HLA typing and the collected biometric information can be archived in a database, network or other pertinent resource.

As used herein, the term "kit" refers to any delivery system for delivering materials. In the context of reaction assays, such delivery systems include systems that allow for the storage, transport, or delivery of reaction reagents (e.g., oligonucleotides, enzymes, primer set(s), etc. in the appropriate containers) and/or supporting materials (e.g., buffers, written instructions for performing the assay etc.) from one location to another. For example, kits can include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be delivered to the intended recipient together or separately. For example, a first container may contain an enzyme for use in an assay, while a second container contains oligonucleotides. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Reference will now be made to various embodiments, examples of which are illustrated in the accompanying drawings.

In accordance with the embodiments, there is disclosed a biometric data collection system having a first component adapted to obtain a representation of an appendage of an individual, and at least a second component comprising a substrate adapted to receive a biological sample from the individual, wherein either the substrate or a biological sample collection device comprising the substrate is labeled with the representation. The first component has a surface adapted to obtain an impression of the appendage and an imaging system is operatively coupled to the surface, wherein the imaging system is configured to collect an electronic image resulting from the impression. The imaging system can be either an optical imaging system or a capacitive scanning/imaging system. The collection system can also have a processor configured to convert the electronic image from the impression into the representation of the appendage. Additionally, the processor can provide for and tie the system in with an outside connections module to networks, software sources, databases of such entities as the FBI, Homeland Security, investigative agencies, intelligence agencies, watch lists, cable systems, the web, optical fiber systems, wireless communications such as satellites, cell phone systems (e.g., GSM), and other pertinent resources. Additionally, the processor can have a database connect to the processor and a connection module connected to the processor. The representation can be configured for uploading into a network or database and other pertinent archiving and information retrieval and comparison resources. The system can also have a component adapted to label the substrate or the biological sample collection device with the representation to enable matching the biometric characteristic to the biological sample. The representation can be graphical, digital, photographic, analog, alphanumeric, hexadecimal or binary, including a barcode. The impression obtained by the system can be converted into an electronic image and the appendage can be a finger, thumb, hand, toe or foot placed upon a surface such as a platen that is transparent. The resulting impression can be a fingerprint, thumbprint, handprint, toe print or footprint.

In accordance with the embodiments, there is also disclosed a method for matching collected biometric information comprising: providing a surface for obtaining a representation of an appendage of an individual, wherein an impression of a fingerprint of a finger of the individual is obtained when the individual touches the surface; converting the fingerprint impression to an electronically readable representation; labeling a biological sample collection device with the electronically readable representation; collecting a biological sample from the individual with the labeled biological sample collection device; wherein the electronically readable representation from the fingerprint is matched to the labeled biological sample collection device following collection of the biological sample. The digit can be a finger, thumb, hand, toe or foot placed upon a surface such as a platen that is transparent. The resulting impression can be a fingerprint, thumbprint, handprint, toe print or footprint. The biological sample can be analyzed by genotyping or HLA typing and the collected biometric information can be archived in a database, network or other pertinent resource.

In accordance with the embodiments, there is also disclosed a method for matching collected biometric information comprising: providing a surface for obtaining a representation of an appendage of an individual, wherein an impression of the appendage of the individual is obtained when the individual touches the surface, wherein the appendage is a digit; converting the impression to an electronically readable representation; labeling a substrate with the electronically readable representation; transferring a biological sample from the individual to the substrate; and matching the electronically readable representation from the impression to the labeled substrate following collection of the biological sample. The digit can be a finger, thumb, hand, toe or foot placed upon a surface such as a platen that is transparent. The resulting impression can be a fingerprint, thumbprint, handprint, toe print or footprint. The biological sample can be analyzed by genotyping or HLA typing and the collected biometric information can be archived in a database, network or other pertinent resource.

Those having ordinary skill in the art will understand that many modifications, alternatives, and equivalents are possible. All such modifications, alternatives, and equivalents are intended to be encompassed herein.

EXAMPLE 1

The following procedures are representative of procedures that can be employed for the surface modification of silicon wafers/membrane.

Experiment:

Genotyping of a biological sample using the AmpFISTR® Identifiler Direct PCR Amplification Kit (Applied Biosystems, Foster City, Calif.). A buccal sample was collected by swabbing the inside of an individual's cheek with a Copan® "DNA flocked swab". A 3 cm square FTA® paper (Whatman) was cut out and place on 5 cm square piece of aluminum foil. The swab was placed in the center of the paper and cover with second piece of 5 cm square aluminum foil. Pressure was applied to the swab for 3 seconds to transfer liquid obtained in from the cheek swabbing to the paper. The aluminum foil on top of the swab was removed and discarded. The lower piece of aluminum foil plus damp paper was placed on a heat block at 100 C and dried for 2 minutes. The FTA paper was removed from the heat and was not sealed for archiving. Instead 1.2 mm circles were punched from the paper at the site of the transfer of the liquid and placed into wells containing Identifiler Direct MasterMix, 12.5 uL/well. Add 12.5 uL Identifiler Direct Primer Set. Amplify 26-28 cycles on ABI 9700. The number of cycles is determined in validation experiments for the Identifiler Direct PCR Amplification Kit according to the manufacture's directions. Transfer 1 uL+9 uL formamide/GS500 LIZ® size standard to 3130x/for analysis. Analyze results using GeneMapper ID-X v.1.2 software.

The resulting capillary electrophoresis resulted in a full STR profile with good color balance and interlocus balance.

While the foregoing specification teaches the principles of the present invention, with examples provided for the purpose of illustration, it will be appreciated by one skilled in the art from reading this disclosure that various changes in form and detail can be made without departing from the spirit and scope of the invention.

The invention claimed is:

1. A biometric data collection system comprising:
   a first component comprising a surface adapted to obtain a representation of an appendage of an individual;
   a second component comprising a substrate separate and uncoupled from the surface of the first component, the substrate adapted to receive a biological sample from the individual while separate and uncoupled from the surface of the first component;
   a processor communicatively coupled to the first and second components, wherein the processor is configured to—

(i) identify details of the representation of the appendage obtained by the first component,
(ii) convert the representation of the appendage into an electronically readable form based on the identified details of the appendage of the individual, the electronically readable form being distinct from an electronic image of the appendage, and
(iii) label either the substrate or a biological sample collection device comprising the substrate with the electronically readable form of the representation of the appendage after obtaining the representation of the appendage; and
a third component adapted to provide heat to the substrate after receiving the biological sample.

2. The system of claim 1, wherein the surface of the first component is adapted to obtain an impression of the appendage.

3. The system of claim 2, further comprising an imaging system operatively coupled to the surface, wherein the imaging system is configured to collect an electronic image resulting from the impression.

4. The system of claim 3, wherein the imaging system is an optical imaging system or a capacitive scanning/imaging system.

5. The system of claim 3, wherein the processor is configured to convert the electronic image from the impression into the electronically readable form of the representation of the appendage.

6. The system of claim 5, further comprising:
(i) a database connected to the processor; and
(ii) a connections module connected to the processor.

7. The system of claim 6, wherein the connections module provides the system access to one or more selected from the group consisting of networks, software sources, databases of such entities as investigative and intelligence agencies, watch lists, cable systems, the web, optical fiber systems, wireless communications, and other pertinent resources.

8. The system of claim 2 wherein the surface for obtaining the representation comprises a platen.

9. A method for matching collected biometric information using the biometric data collection system of claim 2, comprising:
using the first component to provide the surface for obtaining the representation of the appendage of the individual, wherein the impression of the appendage is a fingerprint of a finger of the individual and is obtained when the individual touches the surface;
converting the fingerprint impression to the electronically readable representation;
using the second component to label a biological sample collection device with the electronically readable representation;
collecting a biological sample from the individual with the labeled biological sample collection device; wherein the electronically readable representation from the fingerprint is matched to the labeled biological sample collection device following collection of the biological sample.

10. The method of claim 9, further comprising genotyping the biological sample.

11. The method of claim 9, further comprising archiving the collected biometric information.

12. A method for matching collected biometric information using the biometric data collection system of claim 2, comprising:
using the first component to provide the surface for obtaining the representation of the appendage of the individual, wherein the impression of the appendage of the individual is obtained when the individual touches the surface, wherein the appendage is a digit;
converting the impression to the electronically readable representation;
using the second component to label the substrate with the electronically readable representation;
transferring a biological sample from the individual to the substrate; and
matching the electronically readable representation from the impression to the labeled substrate following collection of the biological sample.

13. The method of claim 12, further comprising genotyping the biological sample.

14. The method of claim 12, further comprising archiving the collected biometric information.

15. The system of claim 1, wherein the representation of the appendage comprises a first component and a second component, the first component being a printed representation of a fingerprint, a thumbprint, a handprint, a toe print, or a footprint of the individual, or a part thereof, and the second component comprising the electronically readable form as a graphical, digital, photographic, analog, alphanumeric, hexadecimal, or binary representation.

16. A biometric data collection system comprising:
a first component comprising a surface adapted to interface with an appendage of an individual;
a second component comprising a substrate separate and uncoupled from the surface of the first component, the substrate adapted to receive a biological sample from the individual while separate and uncoupled from the surface of the first component;
a processor communicatively coupled to the first and second components, wherein the processor is configured to—
(i) identify details of the representation of the appendage obtained by the first component,
(ii) convert the representation of the appendage into an electronically readable form based on the identified details of the appendage of the individual, the electronically readable form being distinct from an electronic image of the appendage, and
(iii) label either the substrate or a biological sample collection device comprising the substrate with the electronically readable form of the representation of the appendage after obtaining the representation of the appendage.

17. The system of claim 16, further comprising an imaging system operatively coupled to the first component, wherein the imaging system is configured to collect an electronic image of the appendage.

18. The system of claim 17, wherein the processor is configured to convert the electronic image from the impression into the electronically readable form of the representation of the appendage.

* * * * *